United States Patent [19]
Richard et al.

[11] Patent Number: 5,569,451
[45] Date of Patent: Oct. 29, 1996

[54] PHOTOPROTECTIVE/COSMETIC COMPOSITIONS COMPRISING TRIORGANOSILYLATED BENZOTRIAZOLES

[75] Inventors: Hervé Richard, Villepinte; Madeleine Leduc, Paris; Alain Lagrange, Couvray, all of France

[73] Assignee: L'Oreal, Paris, France

[21] Appl. No.: 555,334

[22] Filed: Nov. 8, 1995

[30] Foreign Application Priority Data

Nov. 8, 1994 [FR] France ................... 94-13394

[51] Int. Cl.⁶ .................. A61K 7/42; C07F 7/10; C07F 7/08
[52] U.S. Cl. .................. 424/59; 424/70.9; 514/937; 514/438; 548/110
[58] Field of Search .................. 548/110; 424/59, 424/70.9; 514/937, 938

[56] References Cited

U.S. PATENT DOCUMENTS 5,089,250   2/1992   Forestier et al. ................. 424/43

FOREIGN PATENT DOCUMENTS 0282294   9/1988   European Pat. Off. .

OTHER PUBLICATIONS

Chemical Abstracts, vol. 113, No. 16, Oct. 15, 1990, Columbus, Ohio; abstract No. 133518y, Nakahara, Y. et al, "Light--Resistant Polymer Composition", p. 52, & JP-A-0,251, 542 (Adeka Argus Chemical Co., Ltd.).

*Primary Examiner*—Patricia L. Morris
*Attorney, Agent, or Firm*—Burns, Doane, Swecker & Mathis, L.L.P.

[57] ABSTRACT

Topically applicable sunscreen/cosmetic compositions well suited for enhanced photoprotection of human skin and/or hair against the damaging effects of UV-A and UV-B irradiation, particularly solar radiation, comprise a photoprotecting effective amount of a novel triorganosilylated benzotriazole compound having the structural formula (1):

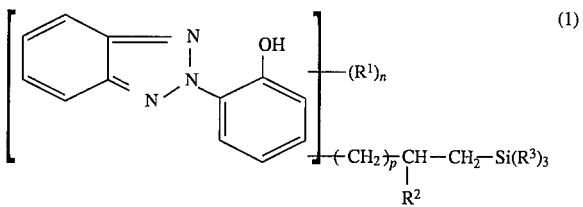

15 Claims, No Drawings

PHOTOPROTECTIVE/COSMETIC COMPOSITIONS COMPRISING TRIORGANOSILYLATED BENZOTRIAZOLES

BACKGROUND OF THE INVENTION

1. Technical Field of the Invention

The present invention relates to novel triorganosilane-substituted benzotriazoles and to novel cosmetic compositions for topical application comprising said triorganosilylated benzotriazoles, for the photoprotection of the skin and/or hair against ultraviolet radiation (such compositions hereinafter sometimes simply designated "sunscreen," "sunscreen/cosmetic" or "photoprotective/sunscreen" compositions).

2. Description of the Prior Art

It is known to this art that light radiation of wavelengths of from 280 nm to 400 nm promotes tanning of the human epidermis, and that irradiation of wavelengths of from 280 to 320 nm, i.e, UV-B irradiation, causes erythema and skin burns which can impair the development of a natural tan; hence, such UV-B radiation must thus be screened from the skin.

It is also known to this art that UV-A radiation, of wavelengths of from 320 to 400 nm, which tans the skin, also adversely affects it, in particular in the event of sensitive skin or skin constantly exposed to solar radiation. UV-A irradiation causes, in particular, a loss in the elasticity of the skin and the appearance of wrinkles, promoting a premature aging thereof. Such irradiation promotes triggering of the erythematous reaction or enhances this reaction in certain individuals, and may even be the source of phototoxic or photoallergic reactions. Thus, it is desirable to also screen out UV-A radiation.

A wide variety of compounds intended for the photoprotection (UV-A and/or UV-B) of human skin are known to this art.

Most of these are aromatic compounds displaying an absorption of UV radiation in the region from 280 to 315 nm or in the region of from 315 to 400 nm, or else in both of these regions together. They are, more often than not, formulated in sunscreen compositions as oil-in-water emulsions (namely, a cosmetically acceptable vehicle, carrier or diluent comprising an aqueous continuous dispersing phase and an oily discontinuous dispersed phase) which contain, at various concentrations, one or more traditional lipophilic and/or hydrophilic organic sunscreen compounds comprising an aromatic function suitable for selectively absorbing harmful or deleterious UV radiation. These sunscreen compounds (and the amounts thereof) are selected as a function of the desired specific sun protection factor (the specific protection factor (SPF) being expressed mathematically by the ratio of the irradiation time required to attain the erythemogenic threshold with the UV screening agent to the time required to attain the erythemogenic threshold in the absence of UV screening agent.)

Other than their sunscreen activity, these compounds having anti-UV properties must also display good cosmetic characteristics in the compositions comprised thereof, good solubility in common solvents, and especially fats such as oils and greases, and also good resistance to water and to perspiration (durability).

Among such prior art aromatic compounds, p-aminobenzoic acid derivatives, benzylidenecamphor derivatives, cinnamic acid derivatives and benzotriazole derivatives are particularly representative. However, certain of these compounds do not display all of the properties required for an acceptable UV screening agent in sunscreen compositions. In particular, their intrinsic screening activity may be insufficient, their solubility in the different formulations employed for photoprotection is not always sufficiently good (fat solubility in particular), they may not possess sufficient stability to light (photostability) and they may also display resistance to water and to sweat. It is also desirable that these sunscreen compositions do not penetrate the skin.

Thus, in the particular case of sunscreen compounds of the benzotriazole type, derivatives thereof have been prepared which have improved properties, especially in respect of their fat solubility and their cosmetic character, by effecting bonding of the benzotriazole screening group via grafting (hydrosilylation) onto a macromolecular chain of the silicone (organopolysiloxane) type. Such derivatives are described in EP-0,392,883, assigned to the assignee hereof, and are generally denominated "silicone screening agents", but the fat-solubility of these compounds can still be inadequate and, furthermore, in order to provide satisfactory sunscreen properties, it is often necessary to employ relatively large amounts of these photoprotective polymers, resulting in poor cosmetic properties in respect of the formulations comprised thereof.

Too, the stability and, notably, the photostability of such compounds remains less than completely satisfactory.

SUMMARY OF THE INVENTION

Accordingly, a major object of the present invention is the provision of novel triorganosilane-substituted benzotriazole sunscreen compounds which display improved properties, in particular in respect of their solubility in fats, as well as regards their cosmetic properties.

Thus, it has now unexpectedly been determined that by bonding, in particular via hydrosilylation, a specific benzotriazole derivative, namely, more especially a benzotriazole compound comprising an ethylenically unsaturated short hydrocarbon chain, to a specific and judiciously selected silane, novel triorganosilane-substituted benzotriazole sunscreen compounds are prepared which avoid or conspicuously ameliorate the above disadvantages and drawbacks of the prior art silicone sunscreens, said novel compounds displaying, in particular, very high sunscreen activity, both in the UV-A range and in the UV-B range, very good solubility in the common organic solvents and notably in fatty substances such as oils, excellent cosmetic properties, very good chemical stability (better resistance to hydrolysis both in acidic and basic media) and very good photochemical stability, rendering same particularly well suited for formulation into photoprotective/cosmetic compositions for protecting the skin and/or the hair against the damaging or deleterious effects of ultraviolet radiation.

Briefly, the present invention features novel silane derivatives of benzotriazoles having the following structural formula (1):

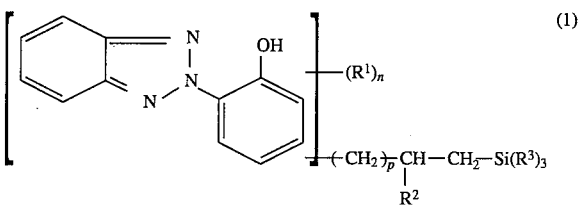

in which n is an integer ranging from 0 to 3, inclusive; the radicals $R^1$, which may be identical or different, are each a $C_1$–$C_8$ alkyl radical; $R^2$ is hydrogen or a $C_1$–$C_4$ alkyl radical; the radicals $R^3$, which may be identical or different, are each a $C_1$–$C_8$ alkyl radical or a phenyl radical; and p is an integer ranging from 0 to 10, inclusive.

DETAILED DESCRIPTION OF BEST MODE AND PREFERRED EMBODIMENTS OF THE INVENTION

More particularly according to the present invention, per the above formula (1), the bonding of the bridging structural unit —(CH$_2$)$_p$—CH(R$^2$)—CH$_2$— to the benzotriazole nucleus, thus ensuring linking of said benzotriazole nucleus to the silicon atom of the triorganosilane, may be effected via any available position presented by the two aromatic ring members of the benzotriazole:

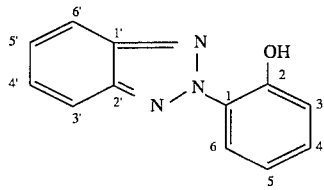

This bonding is preferably via position 3 or 5 (aromatic ring bearing the hydroxyl function) or 4' (benzene ring adjacent to the triazolyl ring), and even more preferably via position 3 or 5.

Similarly, bonding of the substituent radical or radicals $R^1$, when present, may be effected via all other available positions within the benzotriazole. However, such bonding is preferably via position 3, 4' and/or 5.

In the above formula (1), the alkyl radicals can be linear or branched and are advantageously selected from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred alkyl radicals according to the invention are the methyl, ethyl, propyl, n-butyl, n-octyl and 2-ethylhexyl radicals. Even more preferably, the radicals $R^1$ and $R^2$ are methyl radicals.

Among the compounds of the above formula (1), preferred are the random derivatives or well-defined block compounds having at least one, and even more preferably all, of the following definitions:

$R^1$ is methyl $R^2$ is a hydrogen atom or is methyl $R^3$ is methyl, ethyl, isopropyl or isobutyl p is equal to 1.

Exemplary silane derivatives of benzotriazoles according to the present invention include the following:

(a) 2-(2'-hydroxy-5'-methyl-3'-triisobutylsilanylpropylphenyl)-2H-benzotriazole; and (b) 2-[2'-hydroxy-3'-(3-diethylmethylsilanyl- 2-methylpropyl)-5'-methylphenyl]-2H-benzotriazole.

To prepare the compounds of formula (1), a traditional synthesis can be employed, e.g., a hydrosilylation reaction of the type:

starting from the corresponding triorganosilane in which the radical A is replaced by a hydrogen atom. These organosilane derivatives containing SiH functional groups are well known compounds in the silane industry and are generally commercially available.

These triorganosilanes thus correspond to the following formula (2):

in which $R^3$ has the same definition as in the above formula (1).

A standard hydrosilylation reaction is thus conducted between this silane derivative of formula (2), carried out in the presence of a catalytically effective amount of a platinum catalyst, with an organic benzotriazole derivative of the following structural formula (3):

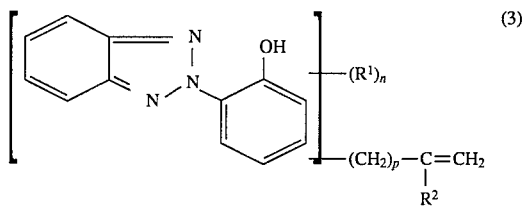

in which $R^1$, $R^2$, n and p have the same definitions as in the above formula (1).

Suitable processes for the preparation of the compounds of formula (3) above are described, in particular, in U.S. Pat. Nos. 4,316,033 and 4,328,346, as well as in the aforementioned EP-A-0,392,883.

In addition, the working conditions to be observed for conducting the hydrosilylation reaction between the compounds of formula (2) and the compound of formula (3) are reported in the aforesaid EP-0,392,883, hereby expressly incorporated by reference.

Relative to the silicone photoprotective agents of the prior art, such as those described in EP 0,392,883, the triorganosilylated benzotriazole sunscreen agents according to the invention exhibit one or more essential structural differences which are the source of their exceptional properties, namely, the fact that, on the one hand, there is only one benzotriazole moiety grafted onto a silicon-containing structural unit, and that, on the other, such silicon-containing structural unit is reduced in this instance to its simplest form, since, according to the invention, it is a monosilane.

Also as indicated above, the compounds of formula (1) above excellent intrinsic screening activity with respect to UV-A and UV-B ultraviolet radiation. In addition, taking account of their highly liposoluble nature, the compounds of formula (1) may be used in high concentrations, thereby imparting very high specific protection factors to the final compositions; moreover, they distribute themselves uniformly in standard cosmetic vehicles comprising at least one fatty phase or at least one cosmetically acceptable organic solvent, and may thus be applied to the skin or hair to form an effective protective film. Too, their cosmetic properties are very good, namely, in particular, compared with the silicone screening agents of the prior art, these products are less sticky and render the skin or hair sofer. Lastly, these products are very stable chemically (they are especially particularly resistant to degradation by hydrolysis which may occur both in acidic and basic media) and photochemically (i.e., they are also resistant to degradation induced by ultraviolet rays).

Thus, the present invention also features cosmetic compositions comprising, in a cosmetically acceptable vehicle, carrier or diluent, preferably including at least one fatty phase or at least one organic solvent, an effective photoprotective amount of at least one compound of the above formula (1).

The compounds of formula (1) are advantageously present in proportions ranging from 0.1% to 20% by weight, and preferably from 0.5% to 10% by weight, relative to the total weight of the composition.

The cosmetic compositions of the invention may be used as compositions for protecting the human epidermis or hair against ultraviolet rays, as sunscreen compositions or as makeup products.

These compositions may, in particular, be in the form of a lotion, a thickened lotion, a gel, a cream, an ointment, a milk, a powder or a solid stick and may optionally be packaged as an aerosol, as a foam, a mousse or a spray.

They can contain the usual cosmetic adjuvants and additives, such as fats and fatty substances, organic solvents, silicones, thickeners, softeners, emollients, complementary sunscreens, anti-foaming agents, moisturizing or hydrating agents, fragrances and perfumes, preservatives, surfactants, fillers, sequestering agents, anionic, cationic, nonionic or amphoteric polymers or mixtures thereof, propellants, basifying or acidifying agents, colorants, dyes, pigments or nanopigments, in particular those designed to provide a complementary photoprotective effect by physically blocking out ultraviolet radiation, or any other ingredient customarily used in cosmetics, especially for the production of sunscreen compositions.

Exemplary of the organic solvents are the lower alcohols and polyols, such as ethanol, isopropanol, propylene glycol, glycerol and sorbitol.

The fats or fatty substances can comprise of an oil or wax or mixtures thereof, fatty acids, fatty acid esters, fatty alcohols, petrolatum, paraffin, lanolin, hydrogenated lanolin or acetylated lanolin. The oils may be selected from among animal, vegetable, mineral or synthetic oils and, in particular, hydrogenated palm oil, hydrogenated castor oil, liquid petrolatum, liquid paraffin, purcellin oil, volatile or non-volatile silicone oils, and isoparaffins.

When the cosmetic composition according to the invention are used for protecting the human epidermis against the deleterious or damaging effects of UV irradiation or as sunscreen compositions, they are advantageously formulated as a suspension or dispersion in solvents or fatty substances, or, alternatively, in the form of an emulsion (in particular of O/W or W/O type, but preferably of O/W type) such as a cream or a milk, or of a vesicle dispersion, or as an ointment, a salve, a gel, a solid stick or an aerosol foam. The emulsions may additionally contain anionic, nonionic, cationic or amphoteric surface-active agents.

When the cosmetic composition according to the invention are used for the photoprotection of the hair, they can be formulated as a shampoo, a lotion, a gel or rinse, to be applied before or after shampooing, before or after dyeing or bleaching, before, during or after permanent-waving or straightening of the hair, or as a styling or treatment lotion or gel, a blow-drying or hair-setting lotion or gel, a hair lacquer, a permanent-waving or hair-straightening composition, or a composition for dyeing or bleaching the hair.

When the cosmetic compositions according to the invention are used as makeup products for the eyelashes, the eyebrows, the skin or the hair, such as a skin-treatment cream, a foundation, a lipstick, an eye shadow, a blush, an eyeliner, a mascara or a coloring gel, they can be formulated in solid or pasty, anhydrous or aqueous form, such as oil-in-water or water-in-oil emulsions, suspensions or gels.

The cosmetic treatment of the skin or hair to protect same against the deleterious effects of ultraviolet radiation, in particular solar radiation, comprising topically applying to the skin or hair an effective amount of a sunscreen/cosmetic composition as described above, or of a compound of the above formula (1).

In order to further illustrate the present invention and the advantages thereof, the following specific examples are given, it being understood that same are intended only as illustrative and in nowise limitative.

EXAMPLE 1

This example relates to the preparation of a compound in accordance with the present invention, having the structural formula:

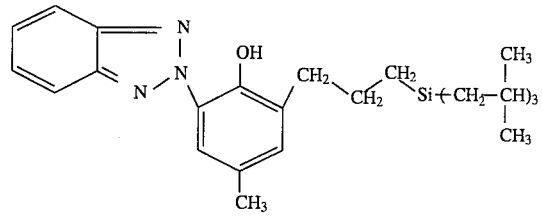

(This compound has formula (1) in which n=1 and $R^1$ is methyl; p=1; $R^2$=H; $R^3$=isobutyl).

20 g (0.075 mol) of 2-allyl-6-benzotriazol-2 -yl-4-methylphenol and 25 ml of dry toluene were introduced into a fully-equipped round-bottomed flask. The mixture was heated to 90° C., under nitrogen. The hydrosilylation catalyst (complex containing 3–3.5% of Pt in cyclovinylmethylsiloxane, marketed by Hüls under the trademark Petrarch PC085: 300 µl) was added, followed by 15.1 g of triisobutylsilane over 1 hour. After boiling for 24 hours under nitrogen, the reaction medium was concentrated. The unreacted starting benzotriazole derivative was filtered off and the unreacted starting silane was distilled off under vacuum (0.2 mmHg). The residue obtained was then chromatographed on silica (eluent: heptane). A fraction of the desired final product, which was in the form of a white powder having a melting point of 80°–82° C., was thus recovered.

The UV absorption characteristics (measured in ethanol) of this compound was as follows:

| | |
|---|---|
| $\gamma_{max}$ : 305 nm | $\epsilon_{max}$ : 15 400 |
| $\gamma_{max}$ : 342 nm | $\epsilon_{max}$ : 14 500 |

This compound is thus a very effective sunscreen which is active in the UV-A and UV-B range.

EXAMPLE 2

This example relates to the preparation of another compound in accordance with the present invention, having the structural formula:

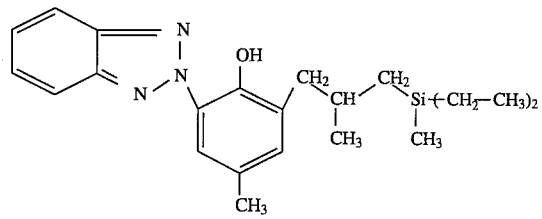

(This compound has formula (1) in which n=1 and $R^1$ is methyl; p=1; $R^2$=methyl; one $R^3$=methyl and two $R^3$=ethyl).

13.97 g (0.05 mol) of 2-benzotriazol-2-yl-4-methyl-6-(2-methylallyl)phenol and 25 ml of dry toluene were introduced into a fully-equipped round-bottomed flask. The mixture was heated to 70° C., under nitrogen. The hydrosilylation catalyst (complex containing 3–3.5% Pt in cyclovinylmethylsiloxane, marketed by Hüls under the trademark Petrarch PC085: 200 µl) was added, followed by addition of 5.37 g (0.0525 mol) of diethylmethylsilane. After 10 hours at 80° C. under nitrogen, the reaction medium was concentrated and chromatography was carried out on silica under pressure (eluent: heptane). A fraction of the desired final product, which was in the form of a white powder having a melting point of 37° C., was thus recovered.

The UV absorption characteristics (measured in ethanol) of this compound were as follows:

| | |
|---|---|
| $\gamma_{max}$ : 304 nm | $\epsilon_{max}$ : 15 520 |
| $\gamma_{max}$ : 343 nm | $\epsilon_{max}$ : 15 050 |

This compound is thus a very effective sunscreen which is active in the UV-A and UV-B range.

EXAMPLE 3

A photoprotective/sunscreen formulation in accordance with the invention was prepared in the form of a sunscreen cream containing:

| | | |
|---|---|---|
| (a) | Compound of Example 1 | 5 g |
| (b) | Mixture of cetylstearyl alcohol and cetylstearyl alcohol oxyethylenated with 33 mol of EO ("SINNOWAX AO" marketed by Henkel) | 7 g |
| (c) | Mixture of non-self-emulsifiable glyceryl mono- and distearate | 2 g |
| (d) | Cetyl alcohol | 1.5 g |
| (e) | $C_{12}$-$C_{15}$ alkyl benzoate ("FINSOLV TN" marketed by Witco) | 20 g |
| (f) | Polydimethylsiloxane | 1.5 g |
| (g) | Glycerol | 17.5 g |
| (h) | Fragrance, preservative | qs |
| (i) | Water | qs 100 g |

This cream was formulated according to the standard techniques for the preparation of emulsions, by dissolving the screening agent in the fatty phase containing the emulsifying agents, heating this fatty phase to about 70°–80° C. and adding, with vigorous stirring, the water which had been heated to the same temperature. Stirring was maintained for 10 to 15 minutes and, after permitting the composition to cool with moderate stirring, the fragrance and preservative were lastly added at about 40° C.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A triorganosilylated benzotriazole compound having the structural formula (1):

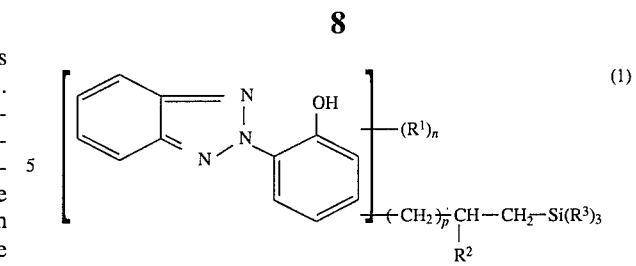

in which n is an integer ranging 0 to 3, inclusive; the radicals $R^1$, which may be identical or different, are each a $C_1$-$C_8$ alkyl radical; $R^2$ is a hydrogen atom or a $C_1$-$C_4$ alkyl radical; the radicals $R^3$, which may be identical or different, are each a $C_1$-$C_8$ alkyl radical or a phenyl radical; and p is an integer ranging from 0 to 10, inclusive.

2. The triorganosilylated benzotriazole compound as defined by claim 1, wherein formula (1), said alkyl radicals are methyl, ethyl, propyl, n-butyl, n-octyl or 2-ethylhexyl radicals.

3. The triorganosilylated benzotriazole compound as defined by claim 1, wherein formula (1), $R^1$ is methyl.

4. The triorganosilylated benzotriazole compound as defined by claim 1, wherein formula (1), $R^2$ is methyl or hydrogen.

5. The triorganosilylated benzotriazole compound as defined by claim 1, wherein formula (1), $R^3$ is methyl, ethyl, isopropyl or isobutyl.

6. The triorganosilylated benzotriazole compound as defined by claim 1, wherein formula (1), p is equal to 1.

7. The triorganosilylated benzotriazole compound as defined by claim 1, wherein formula (1), the radical —$(CH_2)_p$—$CH(R^2)$—$CH_2$— is bonded to the 3-, 4'- or 5-position of the benzotriazole nucleus.

8. The triorganosilylated benzotriazole compound as defined by claim 7, said bonding being to the 3- or 5-position of the benzotriazole nucleus.

9. The triorganosilylated benzotriazole compound as defined by claim 1, wherein formula (1), the readical $R^1$ is bonded to the 3-, 4'- and/or 5-positions of the benzotriazole nucleus.

10. A topically applicable sunscreen/cosmetic composition adopted for the photoprotection of human skin and/or hair, comprising a photoprotecting effective amount of a triorganosilylated benzotriazole compound as defined by claim 1, in a cosmetically acceptable vehicle, carrier or diluent therefor.

11. The sunscreen/cosmetic composition as defined by claim 10, said cosmetically acceptable vehicle, carrier or diluent comprising at least one fatty phase or at least one organic solvent.

12. The sunscreen/cosmetic composition as defined by claim 10, comprising an oil-in-water or water-in-oil emulsion.

13. The sunscreen/cosmetic composition as defined by claim 10, comprising from 0.1% to 20% by weight of said photoprotecting compound.

14. A method for protecting human skin and/or hair against the deleterious effects of ultraviolet irradiation, comprising topically applying thereto an effective amount of the sunscreen/cosmetic composition as defined by claim 10.

15. A method for protecting human skin and/or hair against the deleterious effects of solar radiation, comprising topically applying thereto an effective amount of the sunscreen/cosmetic composition as defined by claim 10.

* * * * *